United States Patent
Huang et al.

(10) Patent No.: US 11,832,895 B2
(45) Date of Patent: Dec. 5, 2023

(54) METHOD AND SYSTEM FOR REGISTER OPERATING SPACE

(71) Applicant: METAL INDUSTRIES RESEARCH & DEVELOPMENT CENTRE, Kaohsiung (TW)

(72) Inventors: Bing-Feng Huang, Kaohsiung (TW); Po-Chi Hu, Kaohsiung (TW); Jin-Yuan Syue, Tainan (TW); Chih-Lung Lin, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 499 days.

(21) Appl. No.: 17/128,228

(22) Filed: Dec. 21, 2020

(65) Prior Publication Data
US 2022/0192751 A1    Jun. 23, 2022

(51) Int. Cl.
*A61B 34/20*   (2016.01)
*G06T 7/33*    (2017.01)
*G06V 10/22*   (2022.01)
*A61B 6/00*    (2006.01)
*A61B 90/00*   (2016.01)

(52) U.S. Cl.
CPC .............. *A61B 34/20* (2016.02); *G06T 7/33* (2017.01); *G06V 10/225* (2022.01); *A61B 6/547* (2013.01); *A61B 2034/2057* (2016.02); *A61B 2034/2065* (2016.02); *A61B 2034/2068* (2016.02); *A61B 2090/3764* (2016.02);
(Continued)

(58) Field of Classification Search
CPC ............ A61B 34/20; A61B 2090/3764; A61B 2090/376; A61B 2034/2057; A61B 2034/2065; A61B 2034/2068; A61B 6/0492; A61B 6/582; A61B 6/547; G06T 7/33; G06T 2207/10148; G06T 2207/30012; G06T 2207/10116; G06K 9/20; G06K 9/2063; G06K 2209/05; G06V 10/225
See application file for complete search history.

(56) References Cited

U.S. PATENT DOCUMENTS

| | | |
|---|---|---|
| 6,351,659 B1 | 2/2002 | Vilsmeier |
| 10,182,872 B2 | 1/2019 | Chang et al. |

(Continued)

FOREIGN PATENT DOCUMENTS

| | | |
|---|---|---|
| TW | I572316 B | 3/2017 |
| TW | I578953 B | 4/2017 |

(Continued)

*Primary Examiner* — Jurie Yun
(74) *Attorney, Agent, or Firm* — CKC & Partners Co., LLC

(57) ABSTRACT

A system for register operating space includes a first positioning mark, a local camera, a second positioning mark, a global camera and a computer system. The first positioning mark is set on a patient. The local camera captures a first image covering the first positioning mark. The second positioning mark is disposed on the local camera. The global camera captures a second image covering the second positioning mark. The focal length of the global camera is shorter than the focal length of the local camera. The computer system is communicatively connected to the local camera and the global camera to provide a navigation interface based on the first image and the second image.

8 Claims, 3 Drawing Sheets

(52) U.S. Cl.
CPC ............ *G06T 2207/10116* (2013.01); *G06T 2207/10148* (2013.01); *G06T 2207/30012* (2013.01); *G06V 2201/03* (2022.01)

(56) References Cited

U.S. PATENT DOCUMENTS

| | | | |
|---|---|---|---|
| 11,350,995 B2 * | 6/2022 | Finley | ................... A61B 34/25 |
| 11,553,969 B1 * | 1/2023 | Lang | ................... G06T 7/0012 |
| 2007/0270660 A1 | 11/2007 | Caylor, III et al. | |
| 2018/0092699 A1 | 4/2018 | Finley | |

FOREIGN PATENT DOCUMENTS

| | | |
|---|---|---|
| TW | I586327 B | 6/2017 |
| TW | I605789 B | 11/2017 |

* cited by examiner

METHOD AND SYSTEM FOR REGISTER OPERATING SPACE

BACKGROUND

Field of Invention

The present disclosure relates to a system and a method for registering operating space by a local camera and a global camera.

Description of Related Art

With the increase of aging population and the influence of modern life characteristics such as obesity, sedentary, etc., diseases of spine lesions are increasing year by year. If conservative treatment fails, it is often necessary to rely on implants to reduce pain and maintain basic functions. The spine is responsible for protecting the central nervous system, but the portion where the implants that can be applied are quite narrow. For example, a pedicle screw may damage the central nervous system. Although an orthopedic minimally invasive surgery is available in the market, how to accurately track the position of the spine during the surgery is still an issue since the position of the spine changes with the patient's posture.

SUMMARY

Embodiments of the present disclosure provide a system for registering operating space. The system includes: a first positioning mark configured to be set on a patient; a local camera configured to capture a first image covering the first positioning mark; a second positioning mark disposed on the local camera; a global camera configured to capture a second image covering the second positioning mark, in which a focus length of the global camera is shorter than a focus length of the local camera; and a computer system communicatively connected to the local camera and the global camera and configured to provide a navigation interface based on the first image and the second image.

In some embodiments, a calibration procedure includes: capturing, by the local camera, a third image covering the first positioning mark; recognizing, by the computer system, the first positioning mark in the third image to compute a first conversion model between the local camera and the first positioning mark; capturing, by the global camera, a fourth image covering the first positioning mark and the second positioning mark; recognizing, by the computer system, the first positioning mark and the second positioning mark in the fourth image to compute a second conversion model between the global camera and the first positioning mark and compute a third conversion model between the global camera and the second positioning mark; and computing, by the computer system, a fourth conversion model between the local camera and the second positioning mark according to the first conversion model, the second conversion model, and the third conversion model.

In some embodiments, the system further includes an X-ray imaging machine and at least one third positioning mark disposed on the X-ray imaging machine, in which the second image also covers the at least one third positioning mark. The computer system is further configured to recognize the first positioning mark in the first image to compute a fifth conversion model between the local camera and the first positioning mark. The computer system is further configured to recognize the second positioning mark in the second image to compute a sixth conversion model between the global camera and the second positioning mark, and recognize the at least one third positioning mark in the second image to compute a seventh conversion model between the global camera and the X-ray imaging machine. The computer system is further configured to compute an eighth conversion model between the first positioning mark and the X-ray imaging machine according to the fourth conversion model, the fifth conversion model, the sixth conversion model, and the seventh conversion model, and to provide the navigation interface based on the eighth conversion model.

In some embodiments, the X-ray imaging machine is a C-arm X-ray machine including an emitting terminal and a receiving terminal, and the at least one third positioning mark is disposed on the receiving terminal.

In some embodiments, a number of the at least one third positioning mark is greater than 1, and each of the third positioning marks corresponds to an emitting angle of the emitting terminal.

From another aspect, embodiments of the present disclosure provide a method for registering operating space for a computer system. The method includes: capturing, by a local camera, a first image covering a first positioning mark which is configured to be set on a patient; capturing, by a global camera, a second image covering a second positioning mark which is disposed on the local camera, in which a focus length of the global camera is shorter than a focus length of the local camera; and providing a navigation interface based on the first image and the second image.

BRIEF DESCRIPTION OF THE DRAWINGS

The invention can be more fully understood by reading the following detailed description of the embodiment, with reference made to the accompanying drawings as follows.

DETAILED DESCRIPTION

Specific embodiments of the present invention are further described in detail below with reference to the accompanying drawings, however, the embodiments described are not intended to limit the present invention and it is not intended for the description of operation to limit the order of implementation. Moreover, any device with equivalent functions that is produced from a structure formed by a recombination of elements shall fall within the scope of the present invention. Additionally, the drawings are only illustrative and are not drawn to actual size.

The using of "first", "second", "third", etc. in the specification should be understood for identifying units or data described by the same terminology, but are not referred to particular order or sequence.

Figure 1:
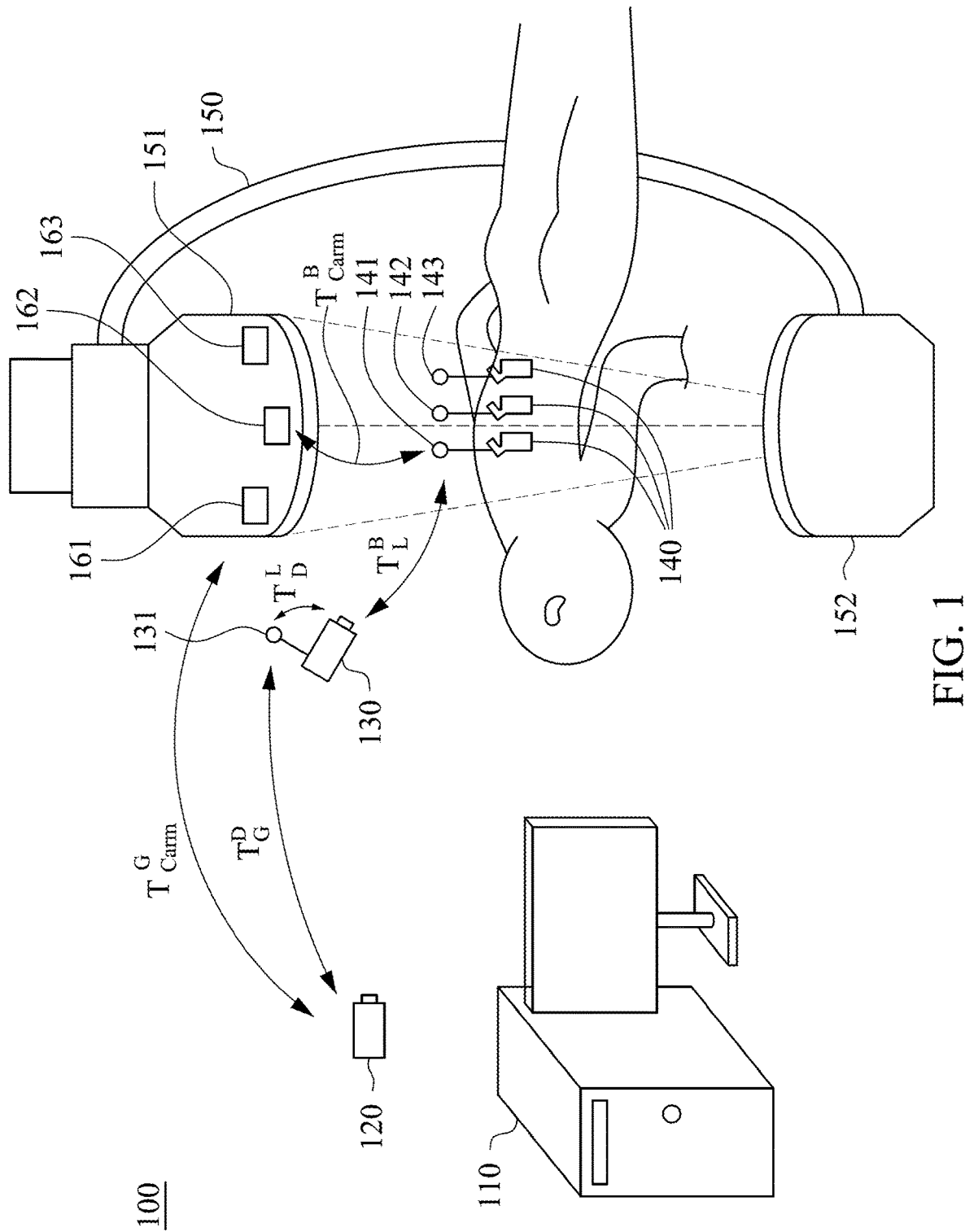
FIG. 1 is a schematic diagram of a system for registering operating space in accordance with some embodiments.

FIG. 1 is a schematic diagram of a system for registering operating space in accordance with some embodiments. Referring to FIG. 1, a system 100 includes a computer system 110, a global camera 120, a local camera 130, a positioning mark 131, positioning marks 141-143, an X-ray imaging machine 150, and positioning marks 161-163.

The global camera 120 and the local camera 130 can capture visible-light images. In some embodiments, the global camera 120 and/or the local camera 130 include an infrared transmitter, an infrared sensor, dual cameras, a structured light sensing device or any device that can sense the depth of the scene.

The positioning marks 141-143 are configured to be set on, for example, a patient's vertebras 140. When the patient's posture changes, the positions of the positioning marks 141-143 change as well. Therefore, the positioning marks 141-143 are used to track the position of the vertebras 140. In other embodiments, the positioning marks 141-143 may be set on another portion of the patient which is not limited in the disclosure. In the embodiment, the positioning marks 141-143 are in the field of the view of the local camera 130. In other words, the local camera 130 can captures images covering the positioning marks 141-143. Each of the positioning marks 141-143 includes one or more special pattern to be recognized. The positioning mark 131 is disposed on the local camera 130 for tracking the position of the local camera 130.

In the embodiment, the X-ray imaging machine is a C-arm X-ray machine which includes an emitting terminal 152 and a receiving terminal 151. The positioning marks 161-163 are disposed on the receiving terminal 151. Emitting angles of X-rays from the emitting terminal 152 can be adjusted. The positioning marks 161-163 correspond to different emitting angles of the emitting terminal 152 respectively.

The positioning mark 131 and the positioning marks 161-163 are in the field of the view of the global camera 120. In other words, the global camera 120 can captures images covering the positioning marks 131, and 161-163. In some embodiments, a focus length of the global camera 120 is shorter than that of the local camera 130. The local camera 130 is used to captures images of the positioning marks 141-143 closely to provide clear images for tracking the positioning marks 141-143. The global camera 120 is used to captures images of the whole scene to determine relative positions of the positioning marks.

The computer system 110 is communicatively connected to the global camera 120 and the local camera 130 by any wire or wireless communication means. The computer system 110 provides a navigation interface based on the images captured by these two cameras. In some embodiments, the navigation interface may be rendered on a screen of the computer system 110, but it may also be rendered on a head mounted device, a tablet or a transparent display which is not limited in the disclosure. Any suitable technology of virtual reality, augmented reality, alternative reality or mixed reality can be used to generate the navigation interface. For example, a computer tomography (CT) image of the patient is captured before surgery, and the spine in the CT image is divided into vertebras by any suitable image processing algorithm to generate corresponding virtual objects. Three of the vertebras correspond to the positioning marks 141-143, and the virtual objects are rendered in the navigation interface. During the surgery, if the positioning marks 141-143 move, the computer system 110 can also move the virtual objects in the navigation interface, and thus the doctor can see the positions of the vertebras without taking X-ray images repeatedly. The images captured by the global camera 120 and the local camera 130 are used to compute the positions of the positioning marks 141-143 (i.e. vertebras 140) in the field. A calibration procedure has to be performed first.

Figure 2:
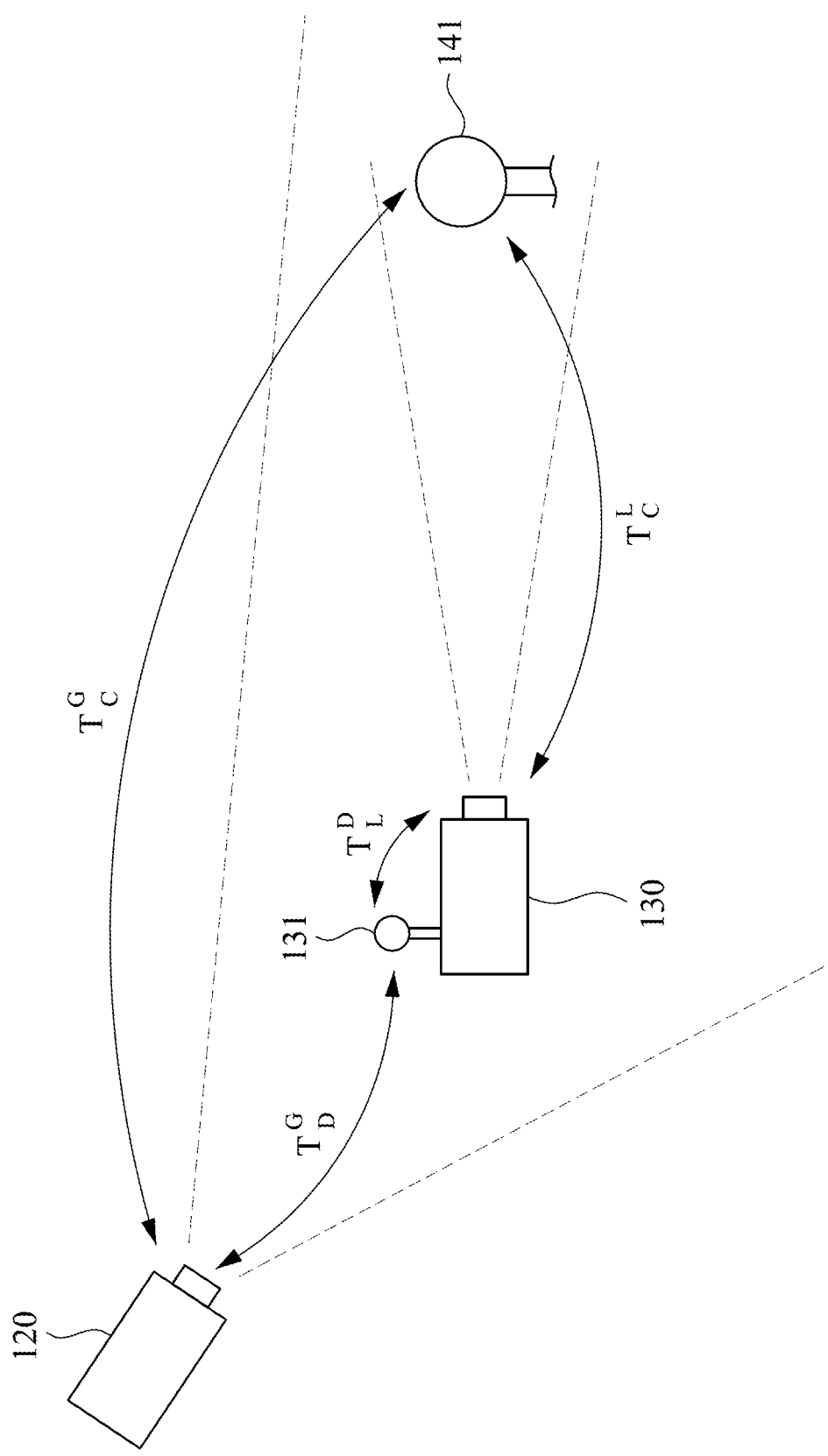
FIG. 2 is a schematic diagram of a calibration procedure in accordance with some embodiments.

FIG. 2 is a schematic diagram of a calibration procedure in accordance with some embodiments. Referring to FIG. 2, the local camera 130 captures an image covering the positioning mark 141, and the computer system recognizes the positioning mark 141 in the image to compute a conversion model $T_C^L$ between the local camera 130 and the positioning mark 141. The conversion model $T_C^L$ is a transformation matrix including information of translation, scaling, shearing, and/or rotating in a 3D space in order to transfer a coordinate system at the positioning mark 141 into a coordinate system at the local camera 130. In detail, coordinates of the positioning mark 141 in the image are transformed into coordinates in the 3D space based on information such as focus of the local camera 130 in the recognition process. The transformation from the image coordinates into the 3D coordinates can be achieved by any suitable computer vision technology or calibration procedure such as capturing images of a rotating disc having special patterns that is not limited in the disclosure. After the recognition process, the 3D coordinates of the positioning mark 141 relative to the local camera 130 are obtained, and these coordinates are used to compute the conversion model $T_C^L$. People in the technical field should be able to adopt any suitable computer vision and image processing algorithms to compute the conversion model $T_C^L$ that is not limited in the disclosure.

The global camera 120 captures an image covering the positioning mark 141 and the positioning mark 131, and then the computer system recognizes the positioning mark 141 and the positioning mark 131 in the image to compute a conversion model $T_C^G$ between the global camera 120 and the positioning mark 141, and to compute a conversion model $T_D^G$ between the global camera 120 and the positioning mark 131. Similarly, the conversion models $T_C^G$ and $T_D^G$ are transformation matrices including information of translation, scaling, shearing, and/or rotating in the 3D space in order to transfer coordinate systems at the positioning mark 141 and the positioning mark 131 into a coordinate system at the global camera 120. The transformation from the image coordinates of the global camera 120 into the 3D coordinates can be achieved by any suitable computer vision technology or calibration procedure.

Note that the position of the positioning mark 131 is not identical to that of the local camera 130, and therefore we need a conversion model $T_L^D$ between the positioning mark 131 and the local camera 130. The conversion model $T_C^G$ between the global camera 120 and the positioning mark 141 can be divided into three parts as the following equation (1). The following equation (2) is derived from the equation (1). In other words, the conversion model $T_L^D$ is computed according to the conversion models $T_D^G$, $T_C^L$ and $T_C^G$.

$$T_C^G = T_D^G \times T_L^D \times T_C^L \qquad (1)$$

$$T_L^D = T_D^{G^{-1}} \times T_C^G \times T_C^{L^{-1}} \qquad (2)$$

In the calibration procedure, the positions of the global camera 120, the local camera 130, and the positioning mark 141 can be set arbitrarily. The relative position between the positioning mark 131 and the local camera 130 is fixed after the calibration procedure is performed.

Referring to FIG. 1, after the calibration procedure is performed, the positions of the positioning marks 141-143 relative to the X-ray imaging machine 150 can be computed. To be specific, taking the positioning mark 162 and the positioning mark 141 as an example, there is a conversion model $T_{Carm}^B$ between the positioning mark 141 and the positioning mark 162 that is divided as the following equation (3).

$$T_{Carm}^B = T_L^B \times T_D^L \times T_G^D \times T_{Carm}^G \qquad (3)$$

The local camera 130 captures an image covering the positioning mark 141, and the conversion model $T_L^B$ is computed by recognizing the positioning mark 141 in the image. The conversion model $T_D^L$ is obtained from the calibration procedure by computing the inverse of the conversion model $T_L^D$. The global camera 120 captures an image covering the positioning mark 131 and the positioning mark 162, and the conversion model $T_G^D$ is computed by recognizing the positioning mark 131 in the image, and the conversion model $T_{Carm}^G$ is computed by recognizing the positioning mark 162 in the image. The conversion model $T_{Carm}^B$ is computed by substituting the conversion models $T_L^B, T_D^L, T_G^D$ and $T_{Carm}^G$ into the equation (3). Therefore, the computer system can provides the navigation interface based on the conversion model $T_{Carm}^B$. For example, a position of the positioning mark 141 relative to the receiving terminal 162 is computed, and then a virtual object of a vertebra is rendered in the navigation interface based on the relative position.

Figure 3:
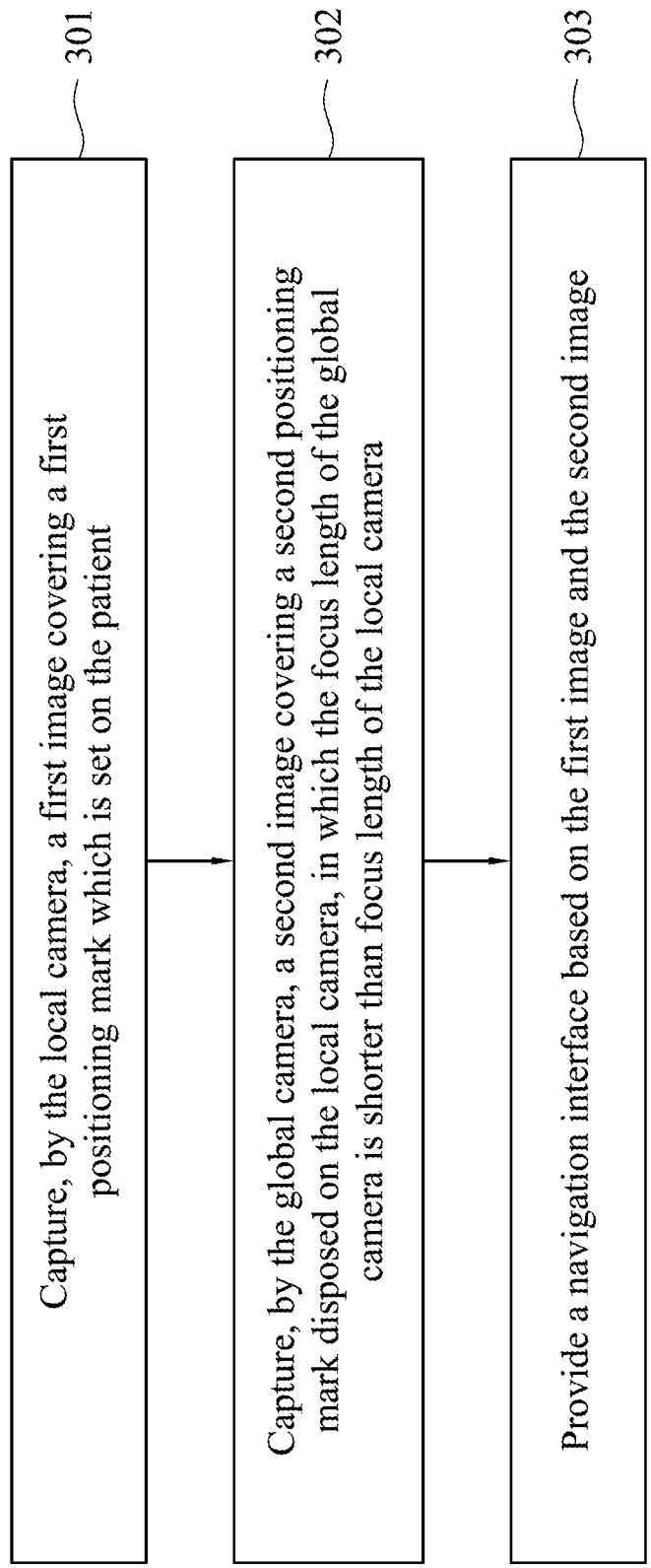
FIG. 3 is a flow chart of a method for registering operating space in accordance with some embodiments.

FIG. 3 is a flow chart of a method for registering operating space in accordance with some embodiments. In step 301, the local camera captures a first image covering a first positioning mark which is set on the patient. In step 302, the global camera captures a second image covering a second positioning mark disposed on the local camera, in which the focus length of the global camera is shorter than focus length of the local camera. In step 303, a navigation interface is provided based on the first image and the second image. However, all the steps in FIG. 3 have been described in detail above, and therefore the description will not be repeated. Note that the steps in FIG. 3 can be implemented as program codes or circuits, and the disclosure is not limited thereto. In addition, the method in FIG. 3 can be performed with the aforementioned embodiments, or can be performed independently. In other words, other steps may be inserted between the steps of the FIG. 3.

In the aforementioned method and system, two cameras are disposed in which the global camera provides images of the whole scene, and the local camera provides clear images for surgery. Therefore, accuracy and filed of the cameras are both ensured at the same time.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A system for registering operating space, the system comprising:
    a first positioning mark configured to be set on a patient;
    a local camera configured to capture a first image covering the first positioning mark;
    a second positioning mark disposed on the local camera;
    a global camera configured to capture a second image covering the second positioning mark, wherein a focus length of the global camera is shorter than a focus length of the local camera; and
    a computer system communicatively connected to the local camera and the global camera and configured to provide a navigation interface based on the first image and the second image,
    wherein a calibration procedure comprises:
        capturing, by the local camera, a third image covering the first positioning mark;
        recognizing, by the computer system, the first positioning mark in the third image to compute a first conversion model between the local camera and the first positioning mark;
        capturing, by the gobal cambera, a fourth image covering the first positioning mark and the second positioning mark;
        recognizing, by the computer system, the first positioning mark and the second positioning mark in the fourth image to compute a second conversion model between the global camera and the first positioning mark and compute a third conversion model between the global camera and the second positioning mark; and
        computing, by the computer system, a fourth conversion model between the local camera and the second positioning mark according to the first conversion model, the second conversion model, and the third conversion mode.

2. The system of claim 1, further comprising:
    an X-ray imaging machine; and
    at least one third positioning mark disposed on the X-ray imaging machine, wherein the second image also covers the at least one third positioning mark,
    wherein the computer system is further configured to recognize the first positioning mark in the first image to compute a fifth conversion model between the local camera and the first positioning mark,
    wherein the computer system is further configured to recognize the second positioning mark in the second image to compute a sixth conversion model between the global camera and the second positioning mark, and recognize the at least one third positioning mark in the second image to compute a seventh conversion model between the global camera and the X-ray imaging machine,
    wherein the computer system is further configured to compute an eighth conversion model between the first positioning mark and the X-ray imaging machine according to the fourth conversion model, the fifth conversion model, the sixth conversion model, and the seventh conversion model, and to provide the navigation interface based on the eighth conversion model.

3. The system of claim 2, wherein the X-ray imaging machine is a C-arm X-ray machine comprising an emitting terminal and a receiving terminal, and the at least one third positioning mark is disposed on the receiving terminal.

4. The system of claim 3, wherein a number of the at least one third positioning mark is greater than 1, and each of the third positioning marks corresponds to an emitting angle of the emitting terminal.

5. A method for registering operating space for a computer system, the method comprising:
    capturing, by a local camera, a first image covering a first positioning mark which is configured to be set on a patient;
    capturing, by a global camera, a second image covering a second positioning mark which is disposed on the local camera, wherein a focus length of the global camera is shorter than a focus length of the local camera; and
    providing a navigation interface based on the first image and the second image; and
    performing a calibration procedure comprising:
        capturing, by the local camera, a third image covering the first positioning mark;

recognizing, by the computer system, the first positioning mark in the third image to compute a first conversion model between the local camera and the first positioning mark;

capturing, by the global camera, a fourth image covering the first positioning mark and the second positioning mark;

recognizing, by the computer system, the first positioning mark and the second positioning mark in the fourth image to compute a second conversion model between the global camera and the first positioning mark and compute a third conversion model between the global camera and the second positioning mark; and computing, by the computer system, a fourth conversion model between the local camera and the second positioning mark according to the first conversion model, the second conversion model, and the third conversion model.

6. The method of claim 5, wherein the second image also covers at least one third positioning mark disposed on an X-ray imaging machine, and the method further comprises:

recognizing the first positioning mark in the first image to compute a fifth conversion model between the local camera and the first positioning mark;

recognizing the second positioning mark in the second image to compute a sixth conversion model between the global camera and the second positioning mark, and recognizing the at least one third positioning mark in the second image to compute a seventh conversion model between the global camera and the X-ray imaging machine; and computing an eighth conversion model between the first positioning mark and the X-ray imaging machine according to the fourth conversion model, the fifth conversion model, the sixth conversion model, and the seventh conversion model, and providing the navigation interface based on the eighth conversion model.

7. The method of claim 6, the X-ray imaging machine is a C-arm X-ray machine comprising an emitting terminal and a receiving terminal, and the at least one third positioning mark is disposed on the receiving terminal.

8. The method of claim 7, wherein a number of the at least one third positioning mark is greater than 1, and each of the third positioning marks corresponds to an emitting angle of the emitting terminal.

* * * * *